United States Patent [19]

Bouillon et al.

[11] 4,327,031
[45] * Apr. 27, 1982

[54] ANTI-SOLAR COSMETIC COMPOSITION

[75] Inventors: Claude Bouillon, Eaubonne; Charles Vayssie, Aulnay-sous-Bois; Francoise Richard, Montreuil-sous-Bois, all of France

[73] Assignee: L'Oreal, Paris, France

[*] Notice: The portion of the term of this patent subsequent to Aug. 21, 1996, has been disclaimed.

[21] Appl. No.: 182,759

[22] Filed: Aug. 29, 1980

Related U.S. Application Data

[60] Division of Ser. No. 947,152, Sep. 29, 1978, Pat. No. 4,250,108, which is a division of Ser. No. 497,469, Aug. 14, 1974, Pat. No. 4,165,336, which is a continuation-in-part of Ser. No. 440,570, Feb. 7, 1974, abandoned.

[30] Foreign Application Priority Data

Feb. 19, 1973 [LU] Luxembourg .................. 67061

[51] Int. Cl.$^3$ ................ C07C 123/00; C07F 3/06; C07C 143/24
[52] U.S. Cl. .................. 260/429.9; 260/511; 260/501.21; 260/501.19; 260/501.14; 260/501.12
[58] Field of Search ............. 260/511, 501.21, 501.19, 260/501.14, 429.9, 501.12

[56] References Cited

U.S. PATENT DOCUMENTS 3,781,417 12/1973 Welters et al. .................. 424/59

OTHER PUBLICATIONS

Shriner et al., JACS, 60, 6314 (1938).
Labruyere et al., C.R. Acad. Sci., Ser. C, 275, 673 (1972).

Primary Examiner—Nicky Chan
Attorney, Agent, or Firm—Cushman, Darby & Cushman

[57] ABSTRACT

An anti-solar cosmetic composition contains as the anti-solar agent a compound of the formula

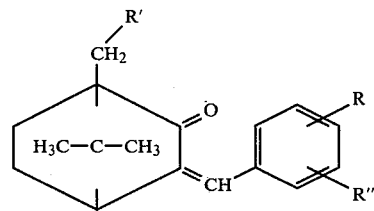

wherein R represents a member selected from the group consisting of hydrogen, a halogen selected from the group consisting of chlorine and fluorine and alkyl containing 1-4 carbon atoms; R' and R" each independently represent a member selected from the group consisting of hydrogen and SO$_3$M wherein M represents a member selected from the group consisting of hydrogen, organic ammonium group and a metal, wherein at least one of R' and R" is other than hydrogen, and R" is a substituent at the para or meta position relative to the bornylidene ring. The anti-solar agent is present in amounts of 0.5–10 percent by weight of said composition.

9 Claims, 1 Drawing Figure

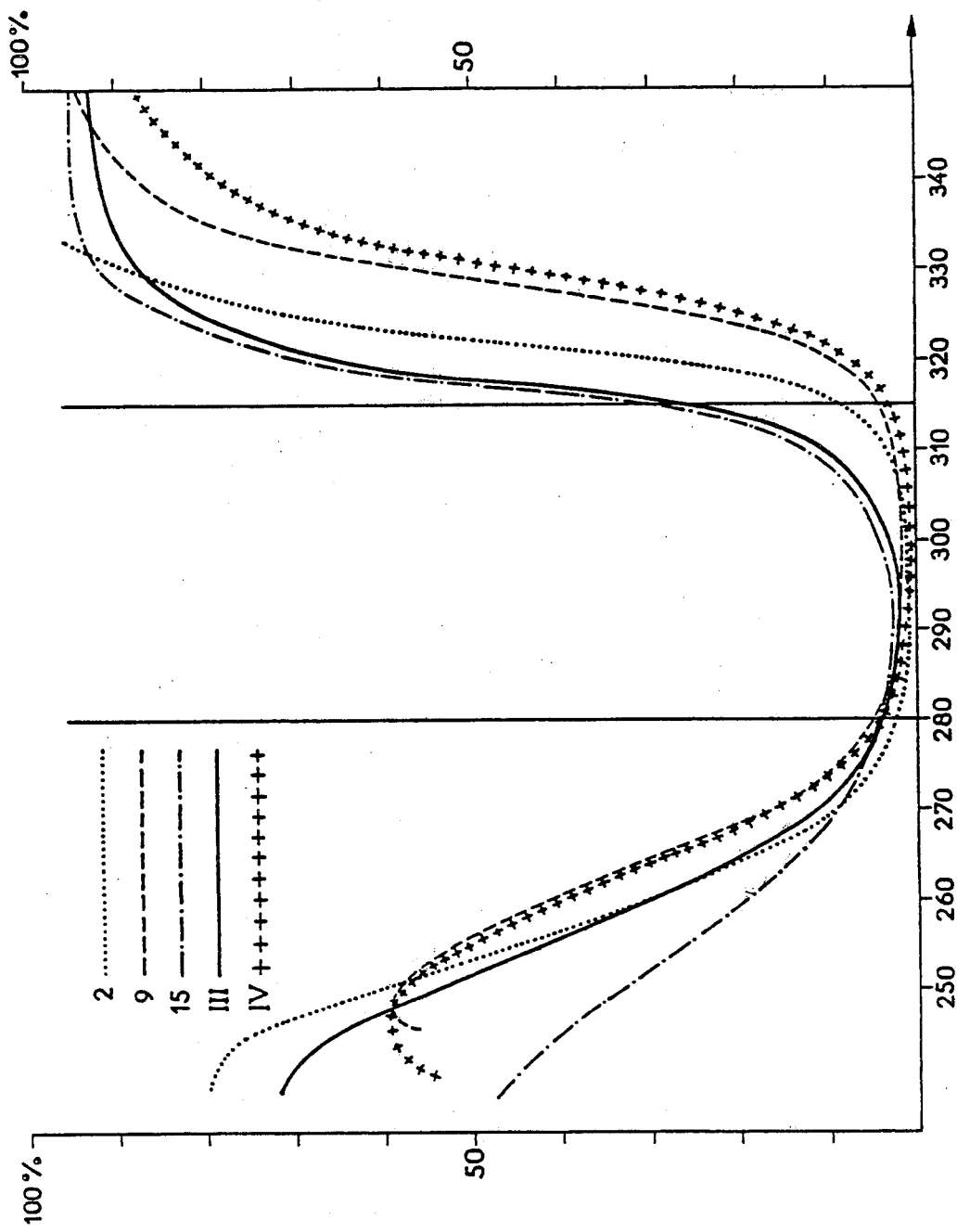

ANTI-SOLAR COSMETIC COMPOSITION

CROSS-REFERENCE TO RELATED APPLICATIONS

This is a divisional of Ser. No. 947,152, filed Sept. 29, 1978, now Pat. 4,250,108 which is a divisional of Ser. No. 497,469, filed Aug. 14, 1974, now U.S. Pat. No. 4,165,336 which is a continuation-in-part of Ser. No. 440,570, filed Feb. 7, 1974, now abandoned and expressly incorporated by reference into Ser. No. 497,469.

The invention relates to new compounds capable not only of absorbing ultra-violet rays of a specific range but also of exhibiting a broad range of solubility in certain solvents or mixtures of solvents. Thus, the novel compounds of the present invention can be incorporated in cosmetic compositions either as an active component, especially when the composition is to be used to protect human skin from harmful effects of actinic rays, or as a preservative for cosmetic preparations susceptible to degradation or discoloration by exposure to light waves.

It is known, for instance, that sunburn, or erythema, results from the excessive exposure to human skin to the rays of the sun and the wave lengths of light in the range of 280-315 millimicrons, often called the "erythematous zone", are those which produce such sunburn. Below this wave length range the sun rays do not present any particular danger, for they are filtered by the ozone in the atmosphere. However, the UV rays which are responsible for or which produce a desirable suntan are those in the zone ranging from 315 to 400 millimicrons.

Consequently, if one desires to be exposed to solar radiation, it is important that the skin be protected with the aid of a composition containing a substance which absorbs the UV rays in the erythematous zone, thereby avoiding an undesirable sunburn, which composition however also transmits those wave lengths in the range of 315 to 400 millimicrons so as to obtain a desirable suntan. In particular, it is necessary to transmit those rays of wave lengths in the neighborhood of 340 millimicrons, which impart maximum browning of the skin without erythema.

Thus, the protective agent must exhibit a high absorbency power between 280-315 millimicrons, and a weak absorbency power above 315 millimicrons. In addition to this critical absorbing power, the protective agent must have other properties and in particular it should exhibit good resistance to the exterior elements, that is, exhibit good photochemical stability, good thermal stability, and have sufficient affinity for the skin and sufficient chemical stability so as not to be removed or degraded by perspiration or at least by washing.

Further, it is also known that certain components and particularly certain dyes often contained in various cosmetic preparations do not always possess sufficient stability to light. These cosmetic compositions are often provided in the form of a solution, emulsion, gel, suspension, aerosol or dispersion, packaged in clear glass or transparent plastic containers and thus can be exposed to light rays not only during use but also during storage. To protect these dyes there is generally incorporated into the preparation containing the same a "protective filter", or a compound capable of filtering light rays, as disclosed, for instance, in French Pat. No. 2,004,142. However, such protective filters often exhibit insufficient solubility in those solvents or cosmetic bases most often employed and thus their use has been considerably limited.

It has also been observed that some essentially colorless cosmetic compositions, for example, colorless nail enamels frequently experience some alteration and turn yellow after prolonged exposure to light.

Thus it has been found that such cosmetic compositions, colored or colorless, can be preserved in storage only for a certain limited period of time, generally in the order only of a few weeks. To overcome these disadvantages, it has been proposed to incorporate in these compositions a compound capable of filtering light rays. Such a compound, however, must not only exhibit good filtering characteristics, but also good stability and a sufficient degree of solubility in the vehicles conventionally employed in these cosmetic compositions. The present invention now provides new compounds having these different criteria which effectively overcome the disadvantages noted above.

Thus it is an object of the present invention to provide a compound of the formula

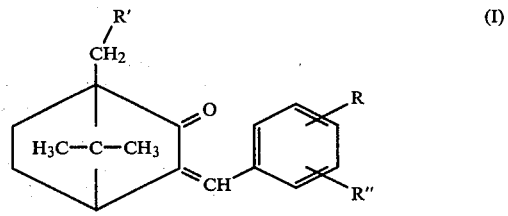

(I)

wherein R represents a member selected from the group consisting of hydrogen; halogen such as Cl or F; and alkyl containing 1-4 carbon atoms; R' and R" each independently represent a member selected from the group consisting of hydrogen and $SO_3M$ wherein M represents a member selected from the group consisting of hydrogen, organic ammonium group and a metal, at least one of R' and R" being other than hydrogen, and R" is a substituent at the para or meta position relative to the bornylidene ring.

The compounds of formula (I) wherein R" is $SO_3M$ are prepared by reacting a compound of the formula

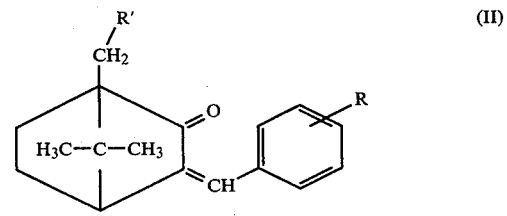

(II)

wherein R and R' have the meanings given above with concentrated sulfuric acid, or oleum or chlorosulfonic acid.

The compounds of formula (II) in turn can be prepared according to the Haller method which consists in condensing an aromatic aldehyde on the sodium salt of camphor, the latter being prepared by reacting camphor with sodium or a strong base such as sodium amide, sodium hydride or a sodium alcoholate. The reaction to produce compounds of formula (II) is preferably performed in an inert solvent such as benzene, toluene or ether, and there are selected as the initial reactants an aldehyde and a camphor derivative suitable for obtaining the desired compound.

It is also an object of the invention to provide compounds of formula (II) in which R' represents SO₃M or when R' represents hydrogen R represents a member selected from the group of fluorine and alkyl containing 2–4 carbon atoms.

The metallic and ammonium salts of formula (I), i.e., the compounds for which R' and/or R" have the value $SO_3M$, wherein M is other than hydrogen can be isolated directly from the reaction medium by treatment with an inorganic base or with a metallic salt such as a sulfate or chloride. These metallic salts can also be obtained easily according to the usual processes by neutralization of the corresponding sulfonic acid with an inorganic base such as a hydroxide, a carbonate or a metallic alcoholate, or alternatively with an organic base such as a primary, secondary or tertiary amine, a quaternary ammonium hydroxide, or an amino acid with a basic character.

Finally, the ammonium salts of formula (I) can also be prepared by cation exchange between a quaternary ammonium halide and the corresponding sulfonic acid of formula (I) which can, if desired, be employed in the form of its sodium salt.

Representative metallic salts of sulfonic acids of formula (I) include, for instance, the sodium, potassium, lithium, calcium, magnesium and zinc salts. Representative organic bases that can be used to prepare an organic ammonium salt of formula (I) include, for instance, monoethanolamine, diethanolamine, triethanolamine, 2-amino-2-methyl propanol, 2-amino-2-methyl-1,3-propanediol, triisopropanolamine, lysine and arginine.

Representative compounds of the present invention include, for instance:

(1) 4-(2-oxo-3-bornylidene methyl) benzene sulfonic acid,
(2) sodium 4-(2-oxo-3-bornylidene methyl) benzene sulfonate,
(3) magnesium 4-(2-oxo-3-bornylidene methyl) benzene sulfonate,
(4) calcium 4-(2-oxo-3-bornylidene methyl) benzene sulfonate,
(5) 4-(2-oxo-3-bornylidene methyl) benzene sulfonate of bis(2-hydroxy ethyl) ammonium,
(6) 4-(2-oxo-3-bornylidene methyl) benzene sulfonate of (1,3-dihydroxy-2-methyl-2-propyl) ammonium,
(7) 2-methyl-5-(2-oxo-3-bornylidene methyl) benzene sulfonic acid,
(8) potassium salt of 2-methyl-5-(2-oxo-3-bornylidene methyl) benzene sulfonic acid,
(9) sodium 2-methyl-5-(2-oxo-3-bornylidene methyl) benzene sulfonic acid,
(10) 4-(2-oxo-3-bornylidene methyl) benzene sulfonate of 5-amino-5-carboxy pentylammonium,
(11) 2-chloro-5-(2-oxo-3-bornylidene methyl) benzene sulfonic acid,
(12) sodium 2-chloro-5-(2-oxo-3-bornylidene methyl) benzene sulfonic acid,
(13) 2-chloro-5-(2-oxo-3-bornylidene methyl) benzene sulfonate of tris-(2-hydroxy ethyl) ammonium,
(14) 3-benzylidene-2-oxo-10-bornane sulfonic acid,
(15) sodium 3-benzylidene-2-oxo-10-bornane sulfonic acid,
(16) 2-chloro-5-(2-oxo-3-bornylidene methyl) benzene sulfonate of tetradecyl trimethylammonium,
(17) 4-(2-oxo-3-bornylidene methyl) benzene sulfonate of benzyl dimethyl hexadecylammonium,
(18) 2-methyl-5-(2-oxo-3-bornylidene methyl) benzene sulfonate of dodecyl pyridinium,
(19) 4-(2-oxo-3-bornylidene methyl) benzene sulfonate of 4-amino-4-carboxy butyl guanidinium and
(2) 2-methyl-5-(2-oxo-3-bornylidene methyl) benzene sulfonate of (1-hydroxy-2-methyl-2-propyl) ammonium.

The compounds of formula (I) exhibit like 3-benzylidene camphor and 3-(4-methyl benzylidene) camphor designated respectively as compounds III and IV, the property of providing remarkable protection to the human skin in the erythematous zone, i.e., in the range of wave lengths of 280 to 315 millimicrons, while at the same time allowing the passage of light rays of wave lengths greater than 315–320 millimicrons, thus providing selective protection as it appears in the attached figure. The compounds of the present invention offer the considerable advantage of having solubility properties that are clearly improved relative to compounds III and IV mentioned above, particularly in aqueous solutions in which these latter are insoluble, in hydroalcoholic solutions and in ethanol.

The attached figure, in which the abscissa indicates the wave lengths in millimicrons and the ordinate indicates the transmission, in percentage of radiations considered, represents the transmission curves 2, 9, 15, III and IV of the following compounds dissolved at a rate of 0.08 millimoles of active product in ethanol:

Compound 2: sodium 4-(2-oxo-3-bornylidene methyl) benzene sulfonate,
Compound 9: sodium salt of 2-methyl-5-(2-oxo bornylidene methyl) benzene sulfonic acid,
Compound 15: sodium salt of 3-benzylidene-2-oxo-10-bornane sulfonic acid,
Compound III: 3-benzylidene camphor and
Compound IV: 3-(4-methyl benzylidene) camphor.

It can be clearly seen that the curves relative to compounds 2, 9 and 15 broadly cover the zone of 280 to 315 millimicrons.

Solubilities were determined in grams of product in 100 ml of solvent represented by water, ethanol and a 50:50 water-ethanol solution for compounds 1 to 7, 9, 14 and 20, and for 3-benzylidene camphor and 3-(4-methyl benzylidene) camphor, designated respectively as III and IV. The following table indicates the results obtained.

| Compound | Water  | Ethanol | Water-Ethanol (50:50) |
|----------|--------|---------|-----------------------|
| III      | Insol. | 14%     | ≦0.5%                 |
| IV       | Insol. | 20%     | <0.1%                 |
| 1        | 100%   | >100%   | 100%                  |
| 2        | 5%     | 0.5%    | 14%                   |
| 3        | 0.1%   | 20%     | 20%                   |
| 4        | 0.2%   | 14%     | 10%                   |
| 5        | 25%    | 25%     | 50%                   |
| 6        | 17%    | 1%      | 33%                   |
| 7        | 4%     | 50%     | 100%                  |
| 9        | 10%    | 3%      | 25%                   |
| 14       | 50%    | 100%    | 100%                  |
| 20       | 50%    | 33%     | 50%                   |

The association of the properties demonstrated by the transmission curve, on the one hand, and by the table of solubilities, on the other, makes it possible to appreciate in a particularly advantageous way the problems and especially the limits of formulation imposed by the use of compounds III and IV, because of their insolubility in an aqueous and hydroalcoholic medium.

The present invention also has for an object a cosmetic composition, stable in regard to light radiations, thus assuring a protection in the range of wave lengths of 280 to 315 millimicrons, but selectively permitting the passage of rays above 315 millimicrons to obtain, under the best conditions, a tanning free of erythema. This composition contains as the agent for protection from light radiations at least one compound of the formula:

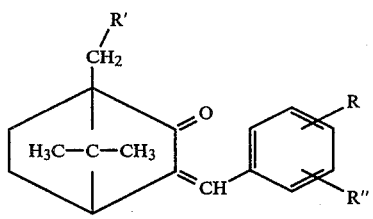

wherein R, R' and R" have the meanings given above.

This composition can be a solution in the form of a lotion, an emulsion in the form of a cream, gel, foam or milk, and generally in all the forms of the usual cosmetic compositions. The compositions can also contain cosmetic adjuvants such as thickeners, softeners, superlubricants, emollients, wetting agents, surfactants, preservatives, antifoam agents, perfumes or any other compatible component usually employed in cosmetics. Finally, the composition of this invention can also contain one or more propellants and be packaged under pressure in an aerosol bomb or container.

The composition of the present invention contains 0.5 to 10% by weight of the compound of formula (I). Representative solvents that can be used include water, lower mono- and polyalcohols and their mixtures or hydro- and oleo-alcoholic solutions. The alcohols employed are, preferably, ethanol, isopropyl alcohol, propyleneglycol, glycerol and sorbitol. Hydroalcoholic mixtures that can be used preferably are mixtures of water and ethyl alcohol wherein ethyl alcohol is present in amounts of about 10–70 percent by weight of said mixture.

The anti-solar composition can be either colorless or colored with dyes and/or pigments usually employed in such compositions, particularly, iron oxides in amounts of about 0.001% to 0.05% by weight of the total weight of the composition.

The present invention also relates to a cosmetic composition whose components are protected from light radiations by the presence of a compound of formula (I) present in an amount of 0.05 to 5% by weight, especially when the said composition contains one or more compounds particularly sensitive to ultraviolet rays. Representative of such sensitive compounds are photosensitive dyes used in amounts of about 0.001% to 0.05% of the total weight of the composition, and triphenylmethane derivatives such as crystal violet, methyl violet, methyl green or Victoria blue BSA.

In addition to the photosensitive dye or dyes and the compound of formula (I), such a composition can also contain a cosmetic film-forming resin, a foaming agent, perfume and other such cosmetic adjuvants.

Representative cosmetic film-forming resins are those having generally a molecular weight ranging from 10,000–700,000 or even higher. Representative cosmetic film-forming agents that can be employed, generally in amounts of 0.5–5 weight percent include polyvinylpyrrolidone having a molecular weight of about 10,000 to 700,000, copolymer of vinylpyrrolidine/vinyl acetate, 70%/30% to 30%/70% having a molecular weight of 40,000–400,000, copolymer of vinyl acetate and an unsaturated carboxylic acid such as a copolymer containing 90% vinyl acetate and 10% crotonic acid having a molecular weight of 45,000 to 70,000; terpolymer of methyl methacrylate (15–25%)/stearyl methacrylate (18–28%) and dimethyl methacrylate (52–62%), and particularly in the proportions of 20%/23%/57%, respectively, and vinyl acetate (75–85%)/allyl stearate (10–20%)/allyloxyacetic acid (3–10%) terpolymer, particularly in proportions of 80%/15%/5%, respectively, copolymer of maleic anhydride and methylvinylether in a molar ratio of preferably 1:1 and having a specific viscosity between 0.1–3.5 when measured at 25° C. and at a concentration of 1 g in 100 cc of methylethyl ketone, and the monoethylester, monoisopropylester of monobutylester of said maleic anhydride, methyl vinyl ether copolymer and copolymer of maleic anhydride and butyl vinyl ether.

Representative examples of cosmetic compositions containing a compound of formula (I) either to protect the photosensitive dye contained in the composition or to avoid their yellowing, include capillary compositions such as hair lacquers, plastifying hair setting lotions, hair treating or disentangling setting lotions, shampoos, dye shampoos, hair dye compositions, fingernail polishes, skin treating creams and base makeups. These compositions can thus be packaged and stored without any risk of alteration, in transparent glass or plastic containers.

Further, the compositions of the present invention can also be provided in the form of an aerosol and be packaged under pressure in an aerosol container together with one or more conventional aerosol propellants such as those known as "Freon" and particularly dichlorodifluoromethane, trichloromonofluoromethane and mixtures thereof.

The present invention also has for an object a process for protecting cosmetic compositions capable of being altered or degraded by light rays which comprises incorporating into these compositions at least one compound of formula (I) in an amount of 0.05 to 5% by weight of said composition.

The following non-limiting examples in which the percentages unless otherwise indicated are by weight will give a better understanding of the present invention.

EXAMPLES OF PREPARATION

Example 1: Preparation of 4-(2-oxo-3-bornylidene methyl) benzene sulfonic acid 120 g of benzylidene camphor (0.5 mole) are added with stirring to 320 ml of oleum containing 20% $SO_3$, the rate of addition being regulated so that the temperature does not exceed 50° C. The stirring is continued for an hour at ambient temperature. The reaction mixture is then slowly poured into 200 ml of ice water and the above sulfonic acid precipitates on cooling. After allowing to stand for several hours at 0° C., the precipitate is filtered, then dissolved in 50 ml of water and reprecipitated by addition of 25 ml of concentrated hydrochloric acid. After filtering and drying in a dessicator in the presence of potash, 104 g of a white powder melting at 100° C. are obtained. This product contains 1.5 moles of crystallization water.

When left in air, the product fixes an additional 1.5 moles of water, the resulting compound thus obtained having the formula $C_{17}H_{20}SO_4.3H_2O$ and the following characteristics:

Mol. weight=374; Acid value=2.68 meq/g. Theory 2.67 meq (Milliequivalent/g).

Elementary analysis: Calculated % C: 54.54; H: 6.95; S: 8.55. Found %: C: 54.79; H: 6.84; S: 8.65.

Example 2: Preparation of sodium 4-(2-oxo-3-bornylidene methyl) benzene sulfonate To a solution of 50 g of acid prepared according to example 1, in 100 ml of water, there are added 7.1 g of anhydrous sodium carbonate. The precipitate obtained is filtered and recrystallized in an 80:20 water-acetone mixture. There are obtained 43 g of white flakes having a melting point of 240° C.

After prolonged drying on phosphoric anhydride, a determination of water indicates the presence of 2 moles of crystallization water. When left in the air, the salt fixes one additional mole of crystallization water.

Example 3: Preparation of magnesium 4-(2-oxo-3-bornylidene methyl) benzene sulfonate of the formula

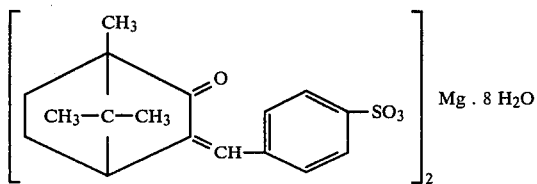

The reaction mixture obtained by reacting 12 g of benzylidene camphor and 32 ml of oleum with 20% $SO_3$ in accordance with the procedures outlined in example 1 is poured into a saturated magnesium chloride solution. After crystallization in a mixture of water and acetone, 7.3 g of white-beige flakes, melting at a temperature above 360° C., are collected.

A determination of water indicates the presence of 8 moles of crystallization water.

Of course, in the case of a metal with "n" valence in place of magnesium, the developed formula would comprise "n" radicals of [4-(2-oxo 3-bornylidene methyl) benzene sulfonate].

Example 4: Preparation of calcium 4-(2-oxo-3-bornylidene methyl) benzene sulfonate Calcium hydroxide is added, until a basic pH is reached, to a solution containing 7.48 g of acid prepared according to example 1 in 15 ml of water. The precipitate is filtered and recrystallized in 80 ml of water. Thus, 5.8 g of a whitish crystalline powder, retaining 5 moles of water per mole of sulfonate, and having a melting point above 360° C., are obtained.

Example 5: Preparation of 4-(2-oxo-3-bornylidene methyl) benzene sulfonate of bis-(2-hydroxy ethyl) ammonium While stirring, 1.05 g of diethanolamine are added to an aqueous solution (10 ml) of 3.74 g of the acid prepared according to Example 1. After evaporation to dryness, a light yellow powder, melting at 85° C., is obtained. The salt obtained retains a mole of water and has the empirical formula $C_{21}H_{31}NO_6S.H_2O$ Elementary analysis: Calculated % C: 56.86; H: 7.50; N: 3.16; S: 7.23. Found % C: 56.48; H: 7.38; N: 3.08; S: 7.51.

Example 6: Preparation of sodium 2-methyl-5-(2-oxo-3-bornylidene methyl benzene sulfonate 25.4 g of 3-p-tolylidene camphor are added to 64 ml of oleum containing 10% $SO_3$, with cooling so as to keep the temperature of the reaction mixture around 35° C. The resulting mixture is then poured into 150 ml of a saturated sodium chloride solution, the mixture being cooled to below 25° C. A precipitate is obtained which is filtered and then washed with a saturated sodium chloride solution. The wet product is made into paste in 70 ml of water. It is then filtered and recrystallized in an 80:20 water-acetone mixture. Thus, 29.3 g of a white powder, melting at 240° C. are obtained.

After drying in a dessicator on phosphoric anhydride, a determination of water indicates the presence of 2 moles of crystallization water.

Example 7: Preparation of 2-methyl 5(-2-oxo-3-bornylidene methyl) benzene sulfonic acid To 8.65 g of sodium salt, prepared according to Example 6 and dissolved in 125 ml of water, there are added 62.5 ml of concentrated hydrochloric acid. The precipitate obtained is filtered and dried on potash to obtain 8 g of a white powder.

This product, crystallized with two moles of water, melts at 130° C. It has the formula $C_{18}H_{22}SO_4.2\ H_2O$ and a molecular weight of 370.

Acid value: 2.63 meq/g; (theory: 2.64 meq/g).

Elementary analysis: Calculated % C: 58.38; H: 7.03; S: 8.65. Found % C: 58.38; H: 6.84; S: 8.62.

Example 8: Preparation of sodium 3-benzylidene-2-oxo-10-bornane sulfonate

A mixture of 37 g of anhydrous camphosulfonic acid and 173 g of sodium methylate in 600 ml of toluene is heated for 1 hour at reflux with stirring. After cooling to ambient temperature, 16.95 g of benzaldehyde are added with stirring. The resulting mixture is heated for 3 hours at reflux and then cooled to ambient temperature at which time there are added thereto 150 ml of water with good stirring. The resulting precipitate is filtered, dried, and then recrystallized in 200 ml of water to obtain, after drying in a dessicator, white flakes (40.55 g) melting at 230° C.

The sodium salt thus obtained contains 0.5 mole of water per mole. When left in the air, it stabilizes after having fixed about 3 moles of crystallization water.

Example 9: Preparation of 3-benzylidene-2-oxo-10-bornane sulfonic acid 20 g of the sodium salt of Example 8 are dissolved with heating in 200 ml of water. 100 ml of concentrated hydrochloric acid are then added with stirring. The precipitate obtained is filtered and dried in a dessicator in the presence of potash and phosphoric anhydride. Thus, 15.3 g of a white powder, melting at 124° C., are obtained. This product contains a mole of crystallization water.

Acid value: (theory: 2.96 meq/g); found 2.95 meq/g.

When left in air, this compound fixes another mole of water to give the empirical formula: $C_{17}H_{20}O_4S.2 H_2O$; (molecular weight: 356).

Acid value: 2.82 meq/g; theory: 2.81 meq/g.

Elementary analysis: Calculated % C: 57.30; H: 6.74; S: 9.07. Found % C: 57.02; H: 6.62; S: 8.99.

Example 10: Preparation of sodium 2-chloro-5-(2-oxo-3-bornylidene methyl) benzene sulfonate There are added, by portions, 274.5 g of 3-p-chlorobenzylidene camphor to 1000 ml of oleum containing 20% by weight of $SO_3$, while maintaining the well stirred mixture at a temperature below 50° C. When the addition has been completed, the resulting reaction mixture is poured into 3 liters of a saturated solution of sodium chloride, while cooling the same. The precipitate formed is filtered and washed with a saturated solution of sodium chloride, then with a little cold water. There are thus obtained 215 g of a whitish powder melting at 260° C.

Determination of water, by the Fischer method, indicates the presence of 3 moles of crystallization water.

Example 11: Preparation of 2-chloro-5-(2-oxo-3-bornylidene methyl) benzene sulfonic acid The salt produced in Example 10 is treated in accordance with the procedures described in Example 7. An oil, which crystallizes slowly, is obtained.

The product thus produced (yield=90%) melts at 140° C. The acid value and determination of water by the Fischer method indicate the presence of 4 moles of crystallization water.

Acid value: Calculated: 2.35 meq/g; Found: 2.36.
Water: Calculated %: 16.9; Found %: 16.9.

Example 12: Preparation of 4-(2-oxo-3-bornylidene methyl) benzene sulfonate of 1,1-bis(hydroxymethyl) ethylammonium The procedures outlined in Example 5 are followed except that the diethanolamine is replaced by 2-amino-2-methyl propane-1,3-diol. There is thus obtained a white powder, melting at 145° C., the solubility of which is 17% by weight in water and 33% by weight in ethanol at 50° C.

Elementary analysis: $C_{21}H_{31}NO_6S$: Calculated % C: 59.29; H: 7.29; N: 3.29; S: 7.53. Found % C: 59.33; H: 7.04; N: 3.38; S: 7.62.

Example 13: Preparation of sodium 3-p-tolylidene-2-oxo-10-bornane sulfonate

The procedures outlined in Example 8 are repeated except that the benzaldehyde is replaced by p-tolualdehyde.

The above product is obtained in the form of light yellow crystals (yield 74%), melting at 190° C. Analysis indicates the presence of 3.5 moles of crystallization water.

Example 14: Preparation of 3-p-tolylidene-2-oxo-10-bornane sulfonic acid

The sodium 3-p-tolylidene-2-oxo-10-bornane sulfonate produced in Example 13 is treated in accordance with the procedures outlined in Example 9. The product obtained contains 1 mole of crystallization water and melts at 220° C.

Acid value: Calculated: 2.82 meq/g; Found: 2.82 meq/g.

Elementary analysis=$C_{18}H_{24}O_4S.H_2O$: Calculated % C: 61.36; H: 6.82; S: 9.09. Found % C: 61.76; H: 6.83; S: 9.11.

Example 15: Preparation of 4-methyl-5-(2-oxo-3-bornylidene methyl) benzene sulfonic acid having the formula

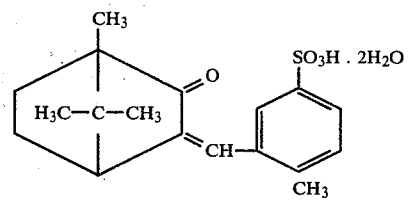

25.4 g of 3-o-methylbenzylidene camphor are dissolved with stirring in 84 ml of oleum containing 20% by weight $SO_3$ with cooling so as to maintain the temperature below 25° C. Stirring of the resulting reaction mixture is continued for an additional 30 minutes at ambient temperature at which time it is poured into 200 ml of crushed ice. The precipitate which forms is filtered and crystallized in 100 ml of acetone to produce white crystals melting at 130° C. and corresponding to the dihydrate.

Acid index: Calculated: 2.70 meq/g; Found: 2.74 meq/g.

Elementary analysis: $C_{18}H_{22}O_4S.2H_2O$: Calculated, % C: 58.38; H: 7.03; S: 8.65. Found, % C: 58.36; H: 6.97; S: 8.46.

Example 16: Preparation of zinc 4-(2-oxo-3-bornylidene methyl) benzene sulfonate of the formula

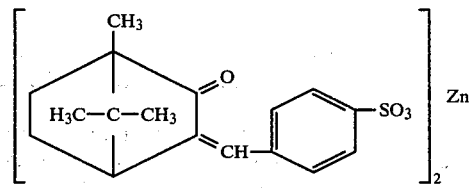

37.4 g of 4-(2-oxo-3-bornylidene methyl) benzene sulfonic acid trihydrate and 6.3 g of zinc carbonate are heated in 250 ml of water until dissolution occurs. The resulting solution is then filtered. The above zinc salt which precipitates on cooling is filtered and then crystallized in 400 ml of water. 64.5 g of white crystals are recovered, melting at 250° C.

Determination of water by the Fischer method reveals the presence of 9.5% water, i.e. 4 moles of crystallization water.

Acid index: Calculated: 2.57 meq/g; Found: 2.54 meq/g.

Example 17: Preparation of 4-(2-oxo-3-bornylidene methyl) benzene sulfonate of 4-amino-4-carboxy butyl guanidinium.

18.7 g of 4-(2-oxo-3-bornylidene methyl) benzene sulfonic acid and 8.7 g of arginine are dissolved in water (75 ml). The resulting solution is evaporated to dryness under a vacuum. The residue is ground in a little sulfuric ether and then filtered, yielding thus 25.6 g of a whitish powder melting at 265° C.

Amine Index: Calculated: 2.03 meq/g; Found: 2.05 meq/g. Elementary Analysis: $C_{23}H_{34}N_4O_6S$: Calculated, % N: 11.33; S: 6.48. Found, % N: 11.10; S: 6.55.

EXAMPLES OF COMPOSITIONS

The compounds of formula (I) can be incorporated directly either in a composition for protecting human skin against solar radiations or in a composition containing components sensitive to light. When the compounds of formula (I) are in the form of sulfonic acids, i.e. with R and/or R' being equal to $SO_3H$, they can easily be neutralized to the desired pH with an organic or inorganic base, selected as a function of its particular cosmetic properties and the desired solubility of the resulting compound.

ANTISOLAR COMPOSITIONS

Example A—An antisolar lotion is prepared by admixing the following components:

| | |
|---|---|
| Lanolin | 2.5 g |
| Butylhydroxyanisole | 0.025 g |
| Butylhydroxytoluene | 0.025 g |
| Octyl gallate | 0.0125 g |
| Triglycerides of fatty acids having 8–12 carbon atoms | 40 g |
| Perfume | 1.25 g |
| 3-benzylidene-2-oxo-10-bornane sulfonic acid | 4 g |
| Ethyl alcohol, 96° titer, q.s.p. | 100 g |

Example B—An antisolar lotion is prepared by admixing the following components:

| | |
|---|---|
| Glycerin | 5 g |
| Polyethylene glycol (MW = 400) | 0.5 g |
| Ethoxylated lanolin | 1 g |
| Soluble perfume | 2 g |
| Sodium 2-methyl-5-(2-oxo-3-bornylidene methyl) sulfonic acid | 2 g |
| Ethyl alcohol, 96° titer | 50 g |
| Water, q.s.p. | 100 g |

Example C—An antisolar aerosol spray is prepared by admixing the following components and packaging the same under pressure in an aerosol container:

| | |
|---|---|
| Absolute ethyl alcohol | 30 g |
| Isopropyl myristate | 20 g |
| Castor oil | 2 g |
| Lanolin | 5 g |
| Perfume | 1 g |
| Magnesium-4-(2-oxo-3-bornylidene methyl) benzene sulfonate | 2 g |
| Dichlorodifluoromethane | 40 g |

Example D—An antisolar aerosol foam is prepared by admixing the following components and packaging the same under pressure in an aerosol container:

| | |
|---|---|
| Sipol wax | 3.5 g |
| Vaseline oil | 6 g |
| Isopropyl myristate | 3 g |
| Preservative - "Nipa ester 82521" (mixture of methyl, ethyl, butyl and benzyl esters of hydroxy benzoic acid) | 0.3 g |
| Glycerin | 10 g |
| Perfume | 0.3 g |
| 4-(2-oxo-3-bornylidene methyl) benzene sulfonate of (1,3-dihydroxy-2-methyl-2-propyl) ammonium | 2.5 g |
| Water, q.s.p. | 100 g |

To make the aerosol, 87 g of the solution prepared above are admixed with 13 g of dichlorodifluoromethane.

Example E—An antisolar cream is prepared by admixing the following components:

| | |
|---|---|
| Cetylstearyl alcohol | 2 g |
| Glycerol monostearate | 4 g |
| Cetyl alcohol | 4 g |
| Vaseline oil | 5 g |
| Butyl stearate | 5 g |
| Propylene glycol (MW = 400) | 7 g |
| Silicone oil | 0.125 g |
| Ethylene oxide polymer having a molecular weight of 100,000–1,000,000 - sold under the tradename "Polyox" (0.5%) | 3.5 g |
| Preservative - "Nipa ester 82521" as in Example D | 0.3 g |
| Perfume | 0.4 g |
| 4-(2-oxo-3-bornylidene methyl) benzene sulfonate of bis(2-hydroxy ethyl) ammonium | 4 g |
| Water, q.s.p. | 100 g |

Example F—An antisolar milk is prepared by admixing the following components:

| | |
|---|---|
| Sipol wax | 5 g |
| Vaseline oil | 6 g |
| Isopropyl myristate | 3 g |
| Silicone oil | 1 g |
| Cetyl alcohol | 1 g |
| Glycerin | 20 g |
| Preservative - "Nipa ester 82521" as in Example D | 0.3 g |
| Perfume | 0.3 g |
| 2-methyl-5-(2-oxo-3-bornylidene methyl) benzene sulfonate of (1,3-dihydroxy-2-methyl-2-propyl) ammonium | 3 g |
| Water, q.s.p. | 100 g |

PRESERVATION OF COLORED PRODUCTS

Example G—A colored hair setting lotion for live human hair is prepared by admixing the following components:

| | |
|---|---|
| 4-(2-oxo-3-bornylidene methyl) benzene sulfonic acid | 0.2 g |
| Vinylpyrrolidone-vinyl acetate copolymer, 70%/30% MW = 40,000 | 2 g |
| Victoria blue BSA dye, C.I. 44045 | 0.001 g |
| Ethyl alcohol | 50 g |
| Triethanolamine, q.s.p. pH 7 | |
| Water, q.s.p. | 100 ml |

Example H—A colored setting lotion is prepared by admixing the following components:

| | |
|---|---|
| 2-methyl-5-(2-oxo-3-bornylidene methyl) benzene sulfonic acid | 0.2 g |
| Crotonic acid-vinyl acetate copolymer 10%/90%, MW = 50,000 having a viscosity of 7–9 cps at 35° C. in a 5% solution of tetrachloroethane | 2 g |
| C.I. Basic Violet No. 3, C.I. 42555 | 0.01 g |
| Ethyl alcohol | 50 g |

-continued

| | |
|---|---|
| Triisopropanolamine, q.s.p. pH 7 | |
| Water, q.s.p. | 100 ml |

Example I—A colored setting lotion is prepared by admixing the following components:

| | |
|---|---|
| 2-methyl 5(-2-oxo-3-bornylidene methyl) benzene sulfonic acid | 1.5 g |
| Polyvinyl pyrrolidone K 30 | 3 g |
| methyl violet C.I. 42535 | 0.005 g |
| Ethyl alcohol | 20.0 g |
| Triethanolamine q.s.p. | pH 8 |
| Water q.s.p. | 100 cc |

What is claimed is:

1. (2-oxo-3-bornylidene methyl) benzene sulfonic acid produced by reacting benzylidene camphor with oleum at a temperature not exceeding 50° C. and thereafter cooling the reaction mixture so as to precipitate the resulting sulfonic acid.

2. The sodium salt of (2-oxo-3-bornylidene methyl) benzene sulfonic acid produced by reacting benzylidene camphor with oleum at a temperature not exceeding 50° C., cooling the resulting reaction mixture and thereafter reacting the cooled reaction mixture with an effective amount of anhydrous sodium carbonate so as to precipitate said sodium salt.

3. The magnesium salt of (2-oxo-3-bornylidene methyl) benzene sulfonic acid produced by reacting benzylidene camphor with oleum at a temperature not exceeding 50° C., cooling the resulting reaction mixture and thereafter reacting the cooled reaction mixture with an effective amount of a saturated solution of magnesium chloride so as to produce said magnesium salt.

4. The bis-(2-hydroxyethyl) ammonium salt of (2-oxo-3-bornylidene methyl) benzene sulfonic acid produced by reacting benzylidene camphor with oleum at a temperature not exceeding 50° C., cooling the resulting reaction mixture and thereafter reacting the cooled reaction mixture with a stoichiometric amount of diethanolamine so as to produce said bis-(2-hydroxyethyl) ammonium salt.

5. The zinc salt of (2-oxo-3-bornylidene methyl) benzene sulfonic acid produced by reacting benzylidene camphor with oleum at a temperature not exceeding 50° C., and reacting the reaction mixture with an effective amount of zinc carbonate so as to produce said zinc salt.

6. The 4-amino-4-carboxybutyl guanidinium salt of (2-oxo-3-bornylidene methyl) benzene sulfonic acid produced by reacting benzylidene camphor with oleum at a temperature not exceeding 50° C., cooling the resulting reaction mixture and thereafter reacting the cooled reaction mixture with an effective amount or arginine so as to produce said 4-amino-4-carboxybutyl guanidinium salt.

7. O-methyl-(2-oxo-3-bornylidene methyl) benzene sulfonic acid produced by reacting 3-o-methyl-benzylidene camphor with oleum.

8. The calcium salt of (2-oxo-bornylidene methyl) benzene sulfonic acid produced by reacting benzylidene camphor with oleum at a temperature not exceeding 50° C., cooling the resulting reaction mixture and thereafter reacting the cooled reaction mixture with an effective amount of calcium hydroxide so as to precipitate said calcium salt.

9. The 1,1-bis(hydroxymethyl) ethyl ammonium salt of (2-oxo-3-bornylidene methyl) benzene sulfonic acid produced by reacting benzylidene camphor with oleum at a temperature not exceeding 50° C., cooling the resulting reaction mixture and thereafter reacting the cooled reaction mixture with an effective amount of 2-amino-2-methyl propane-1,3-diol to produce said 1,1-bis(hydroxymethyl) ethyl ammonium salt.

* * * * *